United States Patent [19]

Bademis

[11] Patent Number: 4,659,312

[45] Date of Patent: Apr. 21, 1987

[54] ATTACHMENT AND LOCKING DEVICE FOR A DENTAL PROSTHESIS

[76] Inventor: Johannis Bademis, Junkerstr. 11, 7910 Neu-Ulm/Schwaighofen, Fed. Rep. of Germany

[21] Appl. No.: 795,617

[22] Filed: Nov. 6, 1985

[30] Foreign Application Priority Data

Nov. 7, 1984 [DE] Fed. Rep. of Germany ....... 3440597

[51] Int. Cl.$^4$ ............................................. A61C 13/12
[52] U.S. Cl. ...................................... 433/182; 433/183
[58] Field of Search ............... 433/183, 180, 181, 182, 433/178

[56] References Cited

U.S. PATENT DOCUMENTS 2,593,287  4/1952  Florentini ........................... 433/178

FOREIGN PATENT DOCUMENTS 868047  5/1953  Fed. Rep. of Germany ...... 433/183
3201391  7/1983  Fed. Rep. of Germany ...... 433/182
508804  1/1955  Italy ................................... 433/183

Primary Examiner—John J. Wilson
Attorney, Agent, or Firm—Karl F. Ross; Herbert Dubno

[57] ABSTRACT

A slide connector for the removable attachment of a dental prosthesis to residual dental structure in the mouth of the user has a female member attached to the prosthesis which receives a male member attached to the residual dental structure. A long pin is spring-loaded in the female member and has an enlarged head which engages in a slot of the male member to permit the head to spring into a recess at the end of this slot. By pressing the pin against the force of its loading spring, the connector can be released.

14 Claims, 9 Drawing Figures

ATTACHMENT AND LOCKING DEVICE FOR A DENTAL PROSTHESIS

FIELD OF THE INVENTION

My present invention relates to an attachment and locking device for a dental prosthesis, to a tool for assembling the device and, more particularly, to a slide connector for affixing a dental prosthesis to residual dental structure and utilizing male and female interfitting parts which are slidably interconnected and then locked releasably in place.

BACKGROUND OF THE INVENTION

It is known, e.g. from German open application-Auslegeschrift DE-OS No. 32 01 391, for example, to attach a dental prosthesis, e.g. a plate, to the residual structure in the mouth of the wearer, e.g. at a crown, by a slide-type connection which comprises a slide-forming female member having a cavity in which a male member is form-fittingly received by the sliding action, the two parts being thereupon retained in their engaged position. The securing device can be a locking pin which is inserted transverse to the direction of sliding action which causes engagement.

In the above-mentioned German patent document, the slide connector utilizes a locking pin which is press fitted into passages of both members and, once inserted, cannot be removed readily, so that should removal be required for any reason, material destruction of cosmetic parts concealing the locking pin which has been press-fitted into place may be required.

OBJECTS OF THE INVENTION

It is the principal object of the invention to provide a slide connector for a dental prosthesis which avoids the drawbacks of earlier press-fitted locking devices requiring destruction of cosmetic work in the production of the prosthesis.

Another object of the invention is to provide such a slide connector which can be readily opened even in the finished prosthesis and can thus enable the finished prosthesis to be removed for repair or modification and just as readily replaced and locked in place without damage to the prosthesis or, of course, to the residual dental structure in the mouth.

Yet another object of the invention is to provide such a releasable locking arrangement which nevertheless can securely retain the prosthesis without play in the mouth of the wearer.

SUMMARY OF THE INVENTION

These objects and others which will become apparent hereinafter are attained, in accordance with the invention in a slide connection having male and female members which can be interfitted with a sliding action of the two members in a given direction so that the female member receives the male member in a cavity formed therein, one of these members, preferably the male member, being mountable on the residual dental structure while the female member can form part of the dental prosthesis to be removably inserted in the mouth.

According to the invention, the female member is provided with an axially shiftable locking pin which extends into this cavity and is displaceable transverse to the aforementioned direction and has, at its end within the cavity, an enlarged locking head which can be connected by a narrower neck with the remainder of the locking pin. The locking pin is displaceable on the female member against the force of a restoring spring and is biased into its locking position by the spring which can be received in a compartment of the female member.

The male member which slidably fits into the cavity and has a form-fitting relationship therewith, i.e. is generally of a configuration complementary to the cavity, has a slot open in the aforementioned direction and which terminates in a recess shaped to accommodate this head remote from the open end of the slot.

When the female member is thus slid over the male member, the mouth of the slot can engage around and receive the neck of the pin and the head of the latter, on full insertion, can form-fittingly engage in the recess so that under the spring force the head is anchored in the recess and reverse sliding movement to the two parts is precluded until the pin is displaced, preferably by application of force to the opposite end thereof to thereby dislodge the head from the recess.

The spring-loaded pin and the recess thus forms a detent which indexes the head in the recess to releasably lock the male member in the female member.

The aforementioned end at least of the pin should be accessible even following the finishing operations on the dental prosthesis so that it can be depressed against the force of the spring to open the detent and allow the disengagement of the slide connector. The form-fitting relationship of the head and the recess or seat for this head forms a secure and play-free retention of the slide connector so that reliance upon a friction-tight or tight-fitting connection of the male and female parts can be eliminated and, while the parts can fit relatively snugly together, they can be separated without excessive force.

This is important because it prevents undue strain on the residual dental structure.

Of course, since the sliding connector after opening, can be readily closed and locked again, this has the advantage that the prosthesis can be repeatedly removed for repair or alteration as wear or other need may require.

Both parts of the connector, namely, the male and female parts, can be readily formed by casting or die-casting and can be easily cemented or soldered so that the connector of the invention has a high degree of versatility.

The slide connector of the invention has been found to be especially effective for dental prostheses which must be repeatedly removed and replaced in the mouth, whether for sanitary or comfort reasons or because wear effects must be corrected.

Wear of the connector parts, even when such repeated removal and replacement generally does not pose a problem because there is no sliding between the parts after assembly in use, all play being excluded by the spring-loaded locking pin.

The avoidance of play can be assured in a preferred embodiment of the invention by making the head of the pin tapered or frustoconical with convergence in the direction in which the spring force is applied to the pin and complementarily tapering or inclining flanks of the recess.

According to a preferred embodiment of the invention, the male member is formed with a structure defining the aforementioned compartment which is separated from the cavity receiving the male member by a wall having a hole through which the neck of the pin is slidably guided, this housing structure forming a guide for the pin for the direction of its axial displacement so that canting of the pin is precluded.

The spring is preferably braced against this wall and against the body of the pin which can be provided with an annular recess open toward the wall and in which the spring is received. The spring can then be a compression-type coil spring surrounding the neck of the pin. The aforementioned guide body of the pin can be cylindrical and the housing portions defining the compartment can likewise be cylindrical. With a long cylindrical guide surface between the pin housing structure, the possibility of pentration of contaminants into the cavities through the housing arrangement for the pin and into the region of the spring is minimized.

Naturally, it is also possible to enclose the sleeve forming the housing in the prosthesis and thereby also to enclose the pin, making it accessible only with minor damage to the prosthetic device.

It has been found to be advantageous to form the neck and the guide body in one piece and to attach the head as a separate piece by a screwthread to this neck or shank of the pin. This greatly facilitates assembly of the device since it merely requires pressing the pin inwardly sufficiently to allow the threaded portion to be exposed within the cavity, whereupon the head can be applied.

To secure the head so that it can be screwed onto the pin, a notch or slot can be formed in the periphery of the head into which a tool can be inserted to hold the head in place while the pin is rotated. Apart from this slot, however, the locking head may be rotationally symmetrical about the axis of the pin so that there is no need for concern about relative angular positions with the pin or the head in use.

With respect to the configuration of the male member, it may be noted that the slot at its leading or open end may have only a width corresponding to the diameter of the shank of the locking pin while the recess inwardly from this open end corresponds in size to the diameter of the head. The front portion of the slot can thus widen toward and into the recess which has the diameter of the locking head. However, to permit a camming action to allow locking without other manipulation of the locking pin, I have found it to be advantageous to provide an inclined surface or ramp which defines the slot at least in part and over which the locking head can be guided upon insertion of the male member into the female member, the head then springing behind the ramp or cam structure to become locked in place in the recess. In the opposite direction, however, the ramp can form a steep flank which engages over the head at least in part so that depression of the pin is essential for release.

In this case, at assembly of the connector when the dental prosthesis is emplaced, the pin will be displaced by the camming action against the force of the spring to compress the latter until the head springs behind the camming flanks and is locked in place.

It is advantageous that this ramp be inclined also in the direction of insertion so that the width of the slot increases in a wedge-like fashion to the rear of the slot.

The male member preferably is formed substantially as a rectangular plate while the female member has a cavity shaped with a rectangular configuration to receive this plate and thus a side wall separated by the thickness of the plate and upon one of which the aforementioned sleeve is mounted. The male member can have, in addition, an anchor formation which can allow it to be engaged in the residual dental structure, e.g. a crown, and it is preferred that this anchoring member have a dovetail configuration which is formed unitarily, i.e. in one piece with the plate.

The invention also applies to a tool for mounting the slide connector of the invention and which is provided with a slide element form-fittingly engaging in the cavity of the female member for holding the head in place and retaining it against rotation while the pin is rotated.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
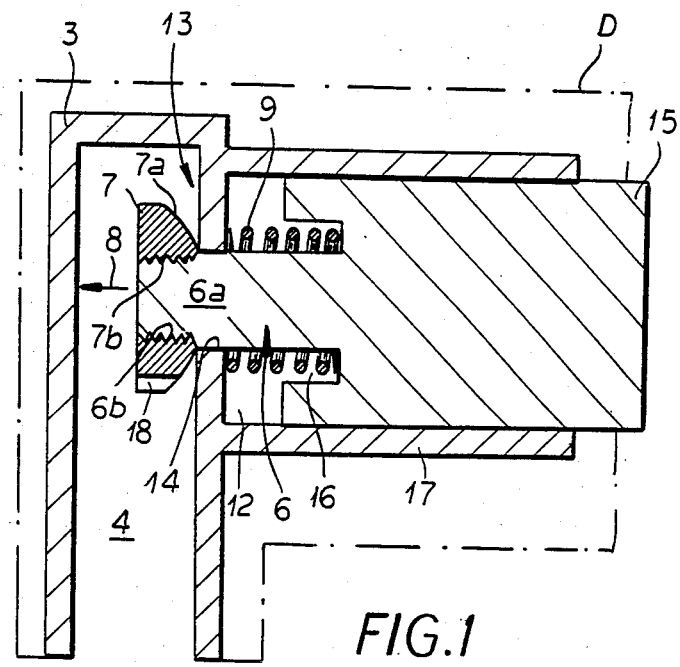
FIG. 1 is a cross section through the female member of a slide connector according to the present invention.
Figure 6:
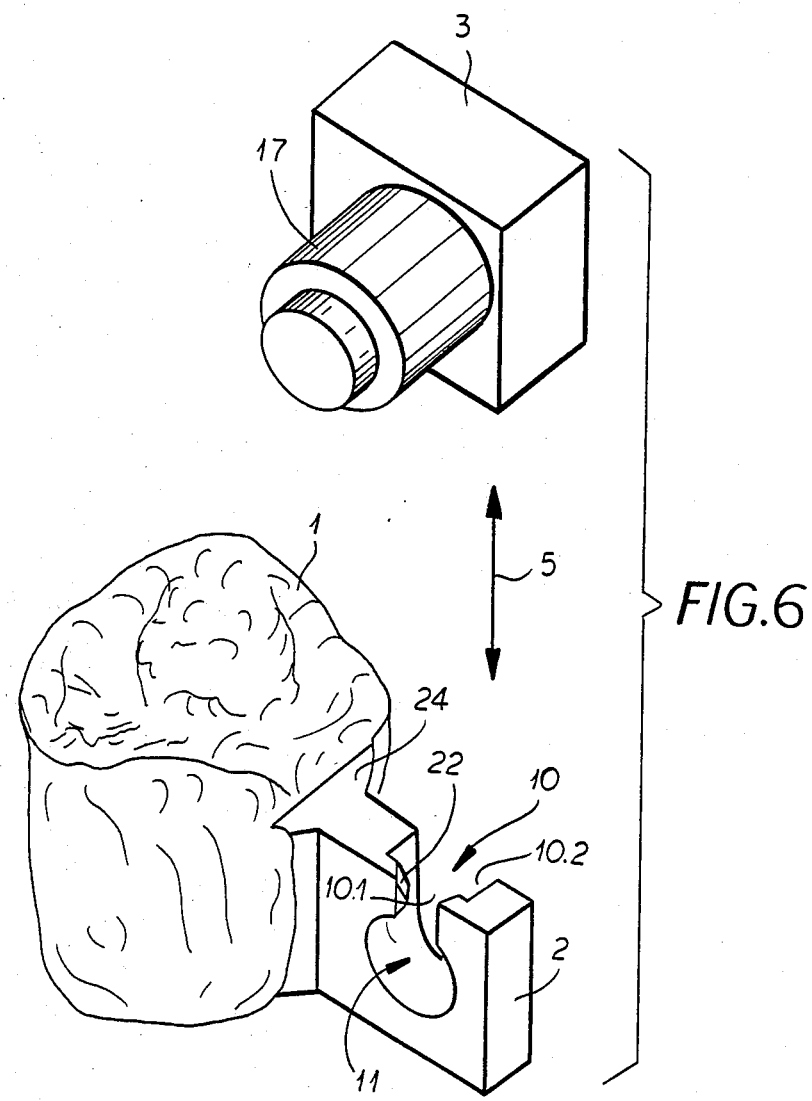
FIG. 6 is an exploded view in perspective and in highly diagrammatic form showing the connector about to be assembled or upon disassembly.

The connector of the present invention has been shown in detail although the dental prosthesis to which the female part is affixed has been represented only by a dot-dash line at D in FIG. 1 while the residual dental structure to which the prosthesis is to be fixed has been depicted in FIG. 6 as a crown 1.

The connector comprises a male part 2 and a female part 3, the latter being capable of complementarily receiving the male part upon mounting of the prosthesis in the mouth.

Figure 2:
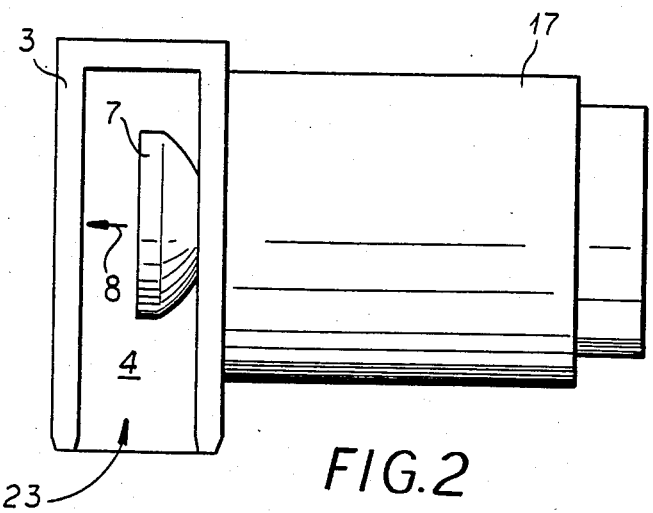
FIG. 2 is an elevational view taken at a right angle to the plane of the section in FIG. 1.
Figure 3:
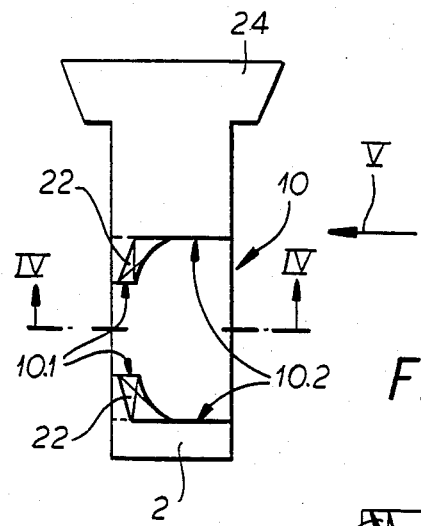
FIG. 3 is a plan view of the male part cooperating with the female part of FIGS. 1 and 2.

Referring, therefore, to FIGS. 1 and 2, it can be seen that the female part 3 is provided as a cavity 4 for the form-fitting receipt of the male part 2 and specifically the plate thereof which will be described in greater detail below.

The given direction in which the two parts are relatively moved for slidable interconnection has been represented by the double-headed arrow 5 and the two parts are locked in place by a spring-loaded locking pin represented generally at 6.

The locking pin 6 is guided so that it is axially shiftable in the female part 3 and carries, in the cavity 4 of the female part, a locking head 7 which is enlarged relative to the pin cross section and the diameter of the shank 6a upon which it is threadedly mounted, in a direction transverse to this pin. As is also apparent from FIG. 1, the head 7 has a flank 7a which is tapered axially in a direction opposite the direction 8 in which the pin 6 can be displaced against the force of a spring 9.

Furthermore, a female thread 7b of the head 7 engages a male thread 6b and the shank 6a to secure the head on the pin.

In the male part 2, there is formed a slot 10 which extends in the direction of insertion (arrow 5) of the male part 2 into the female part 3 and has a width approximately equal to the diameter of the shank 6a of the pin so that as will be described, the head can be cammed in the direction of the arrow 8 to compress the spring 9 further and allow the head to spring into a recess at the end of the slot 10.

Accordingly, the slot 10 is open at the front edge of the male member 2 in the direction of arrow 5 and terminates in the opposite direction in a recess 11 into which the head 7 form-fittingly springs under the force of the spring 9.

The female part 3 of the connector is formed with a guide passage 12 for the pin which is defined by a cylindrical housing wall or boss 17 and to permit this guidance, the pin 6 has a guide body 15 which is also cylindrical and formed in one piece with the shank of the pin and which is slidably guided on the housing wall 15. The guide passage 12 is separated from the cavity 4 by a transverse wall 13 having an opening in which the shank 6a of the pin 6 is slidably mounted.

The spring 9 is braced between this transverse wall 13 and the guide body and is a compression spring which is partly received in an annular recess 16 formed in the body 15 and dimensioned to receive the compressed spring 9 so that the body 15 can abut the wall 13 when this body is pressed fully into the bore 12. The body 15 likewise has a cylindrical configuration.

The locking head 7 is formed at its periphery with a notch 18 which enables this head to be held to permit the head to be screwed to the pin 6.

Figure 7:
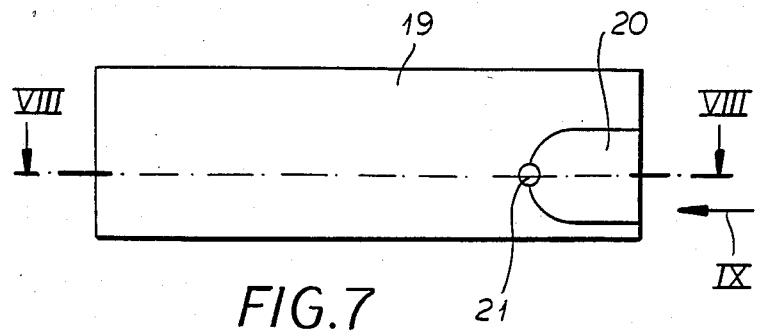
FIG. 7 is a side view of a tool for mounting the locking head of the connector.
Figure 8:
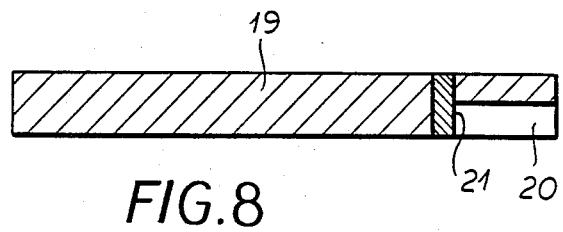
FIG. 8 is a section along the line VIII—VIII of FIG. 7.
Figure 9:
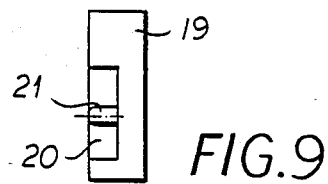
FIG. 9 is an end view of the tool in the direction of the arrow IX in FIG. 7.

For this purpose, I provide a tool as shown in FIGS. 7-9, this tool comprising a slide member or tongue 19 which can be inserted into the recess 4 and is provided and at its open end with a cavity 20 in which the locking head 6 can be snugly received. A projection 21 is disposed at the edge of this recess and can engage in the notch 18 of the head 7.

With the tongue 19 carrying the head 7 and the notch 18 receiving the projection 21, the tongue is inserted into the cavity 4 and because of its dimensions will align the threaded bore 7b of the head with the threaded end 6b of the shank of the pin so that, with rotation of the body 15, the screwthread connection can be made.

Otherwise the locking head 7 is rotationally symmetrical so that it does not have to be aligned with any part of the pin 6 in any particular way after mounting.

The slot 10 in the male member 2 comprises a front part 10.1 with respect to the cross sectional configuration of the slot, whose width corresponds to the width of the shank 6a of the pin, and a rear part 10.2 of the slot whose width corresponds to the diameter of the locking head 7.

In the recess 11, the front part 10.1 of the slot widens to the diameter of the locking head 7.

In a transition between front and rear slot parts 10.1, 10.2, on both sides of the slot, there are formed shoulder surfaces 22 which define ramps in the forward direction over which the tapered portion of the head 7 can ride.

The inclinations of these ramps or camming surfaces formed by the shoulders 22 is such that in the direction of arrow 8, when the connector is assembled, the head 7 is easily cammed until it passes the shoulder and jumps into place. During this operation the spring 9 is progressively compressed and the spring forces thereof increased. The spring force permits the head to jump into place and index the two parts together.

The shoulder surfaces 22 are also inclined in the direction of the slot cross section so that the slot width widens toward the rear part 10.2 in a wedge-like manner. This contour cooperates with the taper of the head 7 to eliminate play when the head is held by sping force against the seat 11 and acts to self-center the parts.

Figure 4:
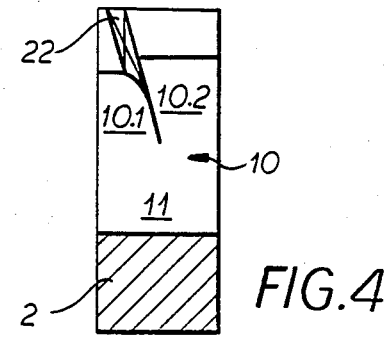
FIG. 4 section taken along the line IV—IV in FIG. 3.
Figure 5:
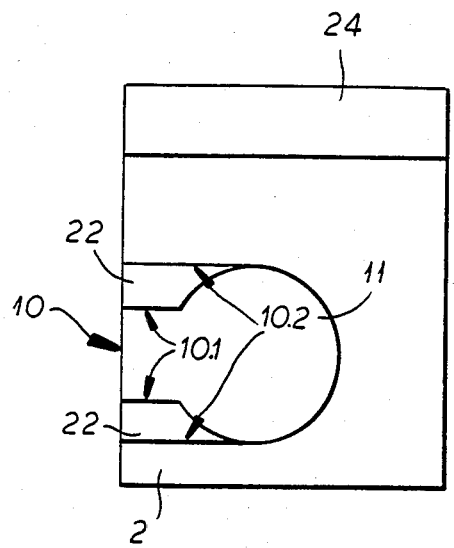
FIG. 5 is a side elevational view in the direcion of arrow V in FIG. 3.

Since there is no equivalent ramp inclined rearwardly and the rear flank of the shoulder is relatively steep (see FIG. 4), the prosthesis cannot be withdrawn with ease unless the pin 6 is depressed by application of pressure to the projecting portion of the guide body 15.

The male member 2 comprises a rectangular plate and the female member 3 is dimensioned to receive this plate and thus has a pair of side walls spaced by the thickness of this plate. One of these side walls carries the sleeve 17 with which it is unitary and formed in one piece.

The housing formed by the female member is open along its small side at 23 parallel to the insertion direction (arrow 5) to allow passage of the anchoring part 24 of the male member 2. This anchoring part 24 can be a dovetail-like formation formed in one piece with the plate of the male member 2 and connected to the crown 1 which represents, as previously indicated, the residual dental structure.

I claim:

1. A slide connector for securing a dental prosthesis to a residual dental structure in a mouth of a wearer, comprising a male member and a female member adapted to slidably receive said male member upon relative displacement of said members in a given direction, one of said members being attachable to said prosthesis and the other of said members being attachable to said residual dental structure, said female member being formed with a cavity adapted to complementarily receive said male member and being provided with an axially displaceable locking pin, said locking pin having a shank and a head enlarged with respect to said shank and disposed in said cavity, said male member having a slot open in said direction and a rear portion defining a recess for form-fittingly receiving said head, whereby a front portion of said slot is dimensioned to enable said shank to slide therethrough, said female member being further provided with a spring acting on said pin and bearing thereon to yieldably retain said head in said recess whereby displacement of said pin against the force of said spring can release said head from said recess.

2. The connector defined in claim 1 wherein said female member is provided with a wall defining said cavity and formed with a passage through which said shank extends, and with guide means on a side of said wall for guiding said pin for axial displacement, said pin being formed on said side of said wall with a guide body engaging said guide means, said spring being braced between said guide body and said wall.

3. The connector defined in claim 2 wherein said body is provided with an annular recess adapted to receive said spring.

4. The connector defined in claim 2 wherein said guide means includes a cylindrical sleeve extending from said wall, said body being cylindrical and guided in said sleeve.

5. The connector defined in claim 2 wherein said body is formed in one piece with said shank, said head being threadedly connected with said shank.

6. The connector defined in claim 5 wherein said head is formed with a notch engageable by a tool to permit screwing said head on said shank.

7. The connector defined in claim 6 wherein the head of said connector is attachable to said shank with a tool, said tool comprising said tool comprising a tongue adapted to extend into said cavity and provided with a recess accommodating said head and with a projection along the periphery of said recess in said tongue for retaining said head against rotation.

8. The connector defined in claim 2 wherein said head is substantially rotationally symmetrical about an axis of said shank.

9. The connector defined in claim 2 wherein said slot has a front slot portion having a width substantially equal to the width of said shank and a rear slot portion of a width substantially equal to the diameter of said head, said front slot portion in said recess widening substantially to the diameter of said head.

10. The connector defined in claim 9 wherein said head tapers in the direction in which said spring biases said pin.

11. The connector defined in claim 10 wherein in a transition region between said portions, shoulder surfaces are formed defining a ramp over which said head is cammed prior to springing into said recess, said surfaces forming a depth of said forward portion of said slot increasing from a minimal thickness to a greatest thickness in the region of said recess.

12. The connector defined in claim 11 wherein said surfaces are also inclined in the slot cross section direction so that the width of said slot widens towards said recess in a wedge configuration.

13. The connector defined in claim 2 wherein said male member comprises a plate-formed anchor portion, said female member having a box configuration open along a small side to pass said anchor portion.

14. The connector defined in claim 13 wherein said anchor portion is formed in one piece with said plate and has a dovetail configuration.

* * * * *